(12) United States Patent
Fujii et al.

(10) Patent No.: US 9,532,720 B2
(45) Date of Patent: Jan. 3, 2017

(54) BLOOD PRESSURE INFORMATION MEASUREMENT DEVICE AND BLOOD PRESSURE INFORMATION MEASUREMENT METHOD

(71) Applicant: OMRON HEALTHCARE Co., Ltd., Kyoto (JP)

(72) Inventors: Kenji Fujii, Hyogo (JP); Tatsuya Kobayashi, Shiga (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 763 days.

(21) Appl. No.: 13/852,132

(22) Filed: Mar. 28, 2013

(65) Prior Publication Data

US 2013/0211268 A1    Aug. 15, 2013

Related U.S. Application Data

(63) Continuation of application No. PCT/JP2011/065967, filed on Jul. 13, 2011.

(30) Foreign Application Priority Data

Sep. 28, 2010  (JP) ................................ 2010-217313

(51) Int. Cl.
   *A61B 5/02*    (2006.01)
   *A61B 5/022*   (2006.01)
   (Continued)

(52) U.S. Cl.
   CPC ........... *A61B 5/02007* (2013.01); *A61B 5/022* (2013.01); *A61B 5/026* (2013.01); *A61B 5/0235* (2013.01);
   (Continued)

(58) Field of Classification Search
   CPC ............ A61B 5/02007; A61B 5/02225; A61B 5/0235; A61B 5/7278; A61B 5/02233; A61B 5/026; A61B 5/022
   See application file for complete search history.

(56) References Cited

U.S. PATENT DOCUMENTS 5,265,011 A *  11/1993  O'Rourke .............. A61B 5/021
                                                    128/920
2004/0167414 A1*  8/2004  Tanabe ...................... A61B 5/02
                                                    600/500
(Continued)

FOREIGN PATENT DOCUMENTS

JP    10-309266 A    11/1998
JP    2004-113593 A    4/2004
(Continued)

OTHER PUBLICATIONS

International Search Report issued in corresponding International Application No. PCT/JP2011/065967 dated Aug. 9, 2011, and English translation thereof (3 pages).
(Continued)

*Primary Examiner* — Tiffany Weston
(74) *Attorney, Agent, or Firm* — Osha Liang LLP

(57) ABSTRACT

A CPU acquires factor information for a degree of arteriosclerosis, stores a plurality of pseudo blood flow waveforms, generates a waveform estimated as a blood flow waveform by compositing the plurality of pseudo blood flow waveforms based on the factor information, decomposes a pulse waveform into waveforms of an ejected wave and a reflected wave using the pulse waveform and the waveform estimated as the blood flow waveform, and calculates an index of the degree of arteriosclerosis from a relationship between the ejected wave and the reflected wave obtained by decomposing the pulse waveform.

13 Claims, 14 Drawing Sheets

(51) Int. Cl.
   *A61B 5/0235*   (2006.01)
   *A61B 5/026*    (2006.01)
   *A61B 5/00*     (2006.01)

(52) U.S. Cl.
   CPC ....... *A61B 5/02225* (2013.01); *A61B 5/02233* (2013.01); *A61B 5/7278* (2013.01)

(56) References Cited

U.S. PATENT DOCUMENTS

| | | |
|---|---|---|
| 2004/0210145 A1 | 10/2004 | Satoh et al. |
| 2009/0030328 A1 | 1/2009 | Harpas et al. |
| 2010/0121203 A1* | 5/2010 | O'Rourke .......... A61B 5/02007 600/483 |

FOREIGN PATENT DOCUMENTS

| | | |
|---|---|---|
| JP | 2004-313468 A | 11/2004 |
| JP | 2009-517140 A | 4/2009 |
| JP | 2009-284966 A | 12/2009 |
| JP | 2010-194108 A | 9/2010 |
| WO | 2009/145027 A1 | 12/2009 |

OTHER PUBLICATIONS

Westerhof et al., "Quantification of Wave Reflection in the Human Aorta From Pressure Alone : A Proof of Principle." Hypertension, Journal of the American Heart Association, Aug. 28, 2006, pp. 595-601 (8 pages).
Patent Abstracts of Japan, Publication No. 2004-113593, Published on Apr. 15, 2004, 1 page.
Patent Abstracts of Japan, Publication No. 2010-194108, Published on Sep. 9, 2010, 1 page.
Patent Abstracts of Japan, Publication No. 2009-284966, Published on Dec. 10, 2009, 1 page.
Patent Abstracts of Japan, Publication No. 2004-313468, Published on Nov. 11, 2004, 1 page.
English abstract of Japanese Publication No. 10-309266 published on Nov. 24, 1998, Espacenet database, 2 pages.

* cited by examiner

BLOOD PRESSURE INFORMATION MEASUREMENT DEVICE AND BLOOD PRESSURE INFORMATION MEASUREMENT METHOD

TECHNICAL FIELD

The present invention relates to a blood pressure information measurement device and a blood pressure information measurement method. In particular, the present invention relates to a blood pressure information measurement device and a blood pressure information measurement method that measure information effective in measuring a degree of arteriosclerosis.

BACKGROUND ART

One existing method for assessing a degree of arteriosclerosis is to measure a pulse wave by compressing a measurement subject's site from outside and assess a degree of arteriosclerosis based on the measured pulse wave. For example, JP 2004-113593A (hereinafter Patent Literature 1) discloses a device including a cuff for measuring a pulse wave and a compression cuff for compressing a portion on the distal side. The device disclosed in Patent Literature 1 measures a pulse wave from the heart while compressing the portion on the distal side so as to separate an ejected wave ejected from the heart from a reflected wave from the bifurcation of the iliac artery and various portions of the artery. The device disclosed in Patent Literature 1 then determines a degree of arteriosclerosis based on indexes such as the difference and the ratio between amplitudes of the ejected wave and the reflected wave, and the difference between times of appearances of the ejected wave and the reflected wave.

In order to detect a degree of arteriosclerosis with high accuracy using the above technique, it is necessary to correctly detect the start point of a reflected wave that appears in a pulse wave. In view of this, for example, JP 2009-517140A (hereinafter Patent Literature 2) discloses a method for separating an ejected wave from a reflected wave using a blood pressure waveform of the aorta and estimated values of a blood flow waveform. FIG. 17A shows one example of a blood pressure waveform. It is considered that the blood pressure waveform of FIG. 17A is obtained by compositing the aforementioned ejected wave and reflected wave as shown in FIG. 17B. According to this method, either a pressure waveform estimated using a transfer function method from a pressure waveform measured in a peripheral artery in an upper body (e.g. a radial artery and a brachial artery), or a pressure waveform measured in a carotid artery, is used as an approximation of the blood pressure waveform of the aorta.

Note that the transfer function method is described in, for example, U.S. Pat. No. 5,265,011 (hereinafter Patent Literature 3). Furthermore, a triangle waveform is used as the blood flow waveform. The triangle waveform is formed by a base, from the start point of a rising edge to the end point of a falling edge of the blood pressure waveform, and a vertex represented by the peak of contraction of the heart, as described in Westerhof, B. E. et al., (Aug. 28, 2006), Quantification of wave reflection in the human aorta from pressure alone: a proof of principle, [online], retrieved May 19, 2010 from http://hyper.ahajournals.org/cgi/reprint/48/4/595 (hereinafter Non-Patent Literature 1).

Patent Literature 1: JP 2004-113593A
Patent Literature 2: JP 2009-517140A
Patent Literature 3: U.S. Pat. No. 5,265,011
Non-Patent Literature 1: Westerhof, B. E. et al. (Aug. 28, 2006). Quantification of wave reflection in the human aorta from pressure alone: a proof of principle, [Online], retrieved May 19, 2010 from http://hyper.ahajournals.org/cgi/reprint/48/4/595.

SUMMARY OF INVENTION

The inventors have measured pulse waves of about 200 measurement subjects, decomposed the pulse waves into ejected waves and reflected waves in accordance with the method described in Patent Literature 2, and calculated traveling times to the reflected waves (Tr) which are the index of a degree of arteriosclerosis. The result of the calculation is shown in FIG. 18. FIG. 18 shows a comparison/relationship between values of Tr calculated in accordance with the method disclosed in Patent Literature 2 (the vertical axis) and estimated values of Tr based on the pulse wave velocity (PWV) measured between the heart and the femoral artery using an existing device (the horizontal axis). Referring to FIG. 18, the square of the correlation coefficient between the Tr values calculated in accordance with the method disclosed in Patent Literature 2 and the estimated values based on the aforementioned PWV ($R^2$) is 0.5368. Judging from this value, it is considered that there is room for improvement in the accuracy of the calculation of Tr in accordance with the method disclosed in Patent Literature 2.

Therefore one or more embodiments of the present invention provide a blood pressure information measurement device and a blood pressure information measurement method that decompose a blood pressure waveform into an ejected wave and a reflected wave in a more correct manner through non-invasive measurement.

A blood pressure information measurement device according to one or more embodiments of the present invention is a blood pressure information measurement device for calculating an index of a degree of arteriosclerosis of a measurement subject as blood pressure information, including a detection member that includes pressure sensors and a central processing unit that detects a pulse waveform by bringing the detection member into contact with an exterior of a measurement site of the measurement subject. The central processing unit acquires factor information for the degree of arteriosclerosis, stores a plurality of pseudo blood flow waveforms, generates a waveform estimated as a blood flow waveform by compositing the plurality of pseudo blood flow waveforms based on the factor information, decomposes the pulse waveform into waveforms of an ejected wave and a reflected wave using the pulse waveform and the waveform estimated as the blood flow waveform, and calculates the index of the degree of arteriosclerosis from a relationship between the ejected wave and the reflected wave obtained by decomposing the pulse waveform.

A blood pressure information measurement method according to one or more embodiments of the present invention is a method for calculating an index of a degree of arteriosclerosis of a measurement subject as blood pressure information in a blood pressure information measurement device. The method includes: a step of detecting a pulse waveform by bringing a detection member that includes pressure sensors into contact with an exterior of a measurement site of the measurement subject; a step of acquiring factor information for the degree of arteriosclerosis; a step of storing a plurality of pseudo blood flow waveforms; a step of generating a waveform estimated as a blood flow waveform by compositing the plurality of pseudo blood flow waveforms based on the factor information; a step of decomposing the pulse waveform into waveforms of an ejected wave and a reflected wave using the pulse waveform and the waveform estimated as the blood flow waveform; and a step of calculating the index of the degree of arteriosclerosis from a relationship between the ejected wave and the reflected wave obtained by decomposing the pulse waveform.

According to one or more embodiments of the present invention, a blood flow waveform for decomposing a pulse waveform into an ejected wave and a reflected wave is estimated by compositing a plurality of pseudo blood flow waveforms using a coefficient obtained from factor information for a degree of arteriosclerosis. As a result, the blood pressure waveform can be decomposed into the ejected wave and the reflected wave in a more correct manner.

DETAILED DESCRIPTION OF INVENTION

Figure 1:
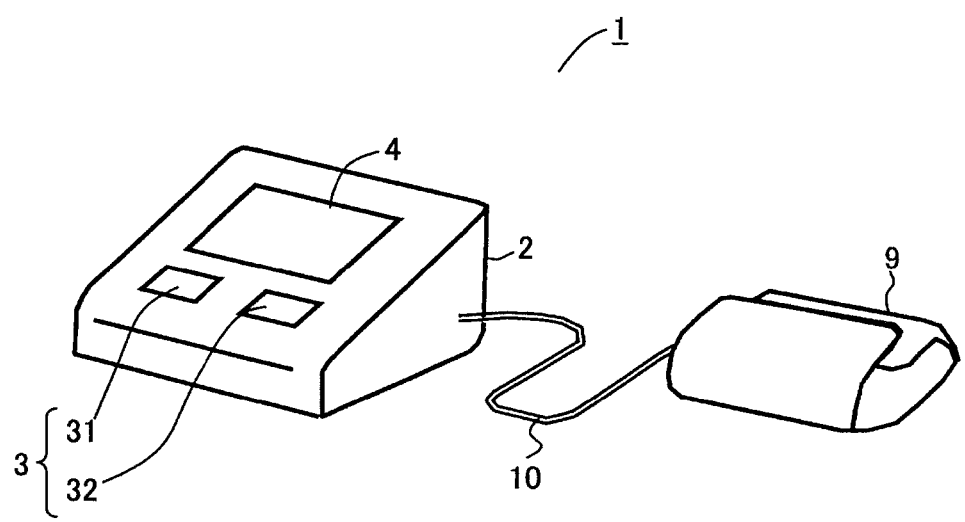
FIG. 1 schematically shows an external view of a blood pressure information measurement device according to one embodiment of the present invention.

The following describes one or more embodiments of the present invention with reference to the drawings. Throughout the following description, the same components and constituent elements are given the same reference numeral. Such components and constituent elements have the same name and functions.

1. Schematic Configuration of Blood Pressure Information Measurement Device

FIG. 1 schematically shows an external view of a blood pressure information measurement device (hereinafter simply referred to as a measurement device) 1, which is a blood pressure information measurement device according to one or more embodiments of the present invention.

Referring to FIG. 1, the measurement device 1 according to one or more embodiments includes a base 2 and an arm band 9 that is worn on an upper arm, i.e. a measurement site. The base 2 and the arm band 9 are connected by an air tube 10. A display unit 4 and an operation unit 3 are arranged on the front face of the base 2. The display unit 4 displays various types of information including the results of measurement. The operation unit 3 is operated so as to issue various types of instructions to the measurement device 1. The operation unit 3 includes switches 31 and 32. The switch 31 is operated to turn on/off the power. The switch 32 is operated to issue an instruction for starting the measurement.

Figure 2A:
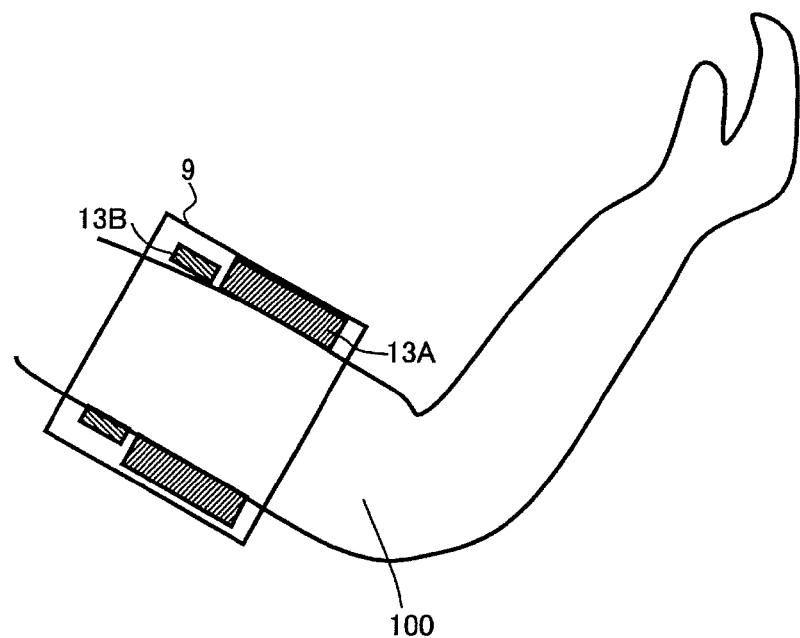
FIG. 2A illustrates a configuration of an arm band shown in FIG. 1.
Figure 2B:
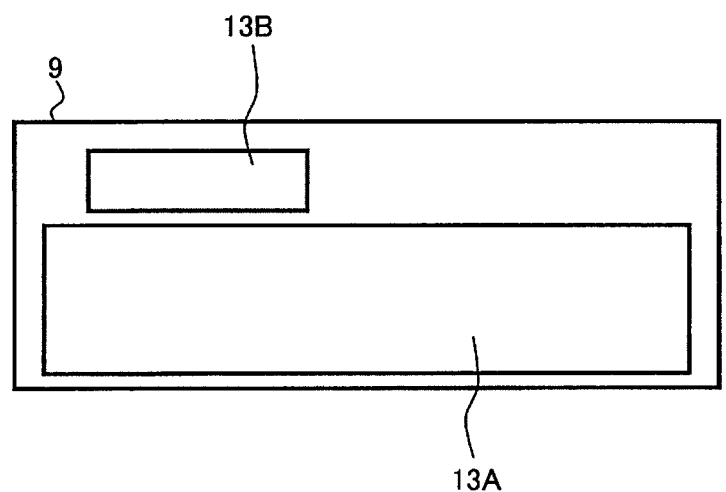
FIG. 2B illustrates a configuration of the arm band shown in FIG. 1.

Referring to FIGS. 2A and 2B, the arm band 9 includes air bladders that serve as fluid bags for compressing a live body. Specifically, the arm band 9 includes air bladders 13A and 13B. The air bladder 13A is a fluid bag used to measure blood pressure as blood pressure information. The air bladder 13B is a fluid bag used to measure a pulse wave as blood pressure information. The size of the air bladder 13B is, for example, approximately 20 mm×200 mm According to one or more embodiments of the present invention, the air capacity of the air bladder 13B is ⅕ of the air capacity of the air bladder 13A or less.

To measure a pulse wave using the measurement device 1, the arm band 9 is wrapped around an upper arm 100, i.e. a measurement site, as shown in FIG. 2A. When the switch 32 is pressed in that state, blood pressure information is measured, and the index for determining a degree of arteriosclerosis is calculated based on the blood pressure information. Note that "blood pressure information" denotes information that is related to blood pressure and measured from a live body. Specific examples of the blood pressure information include a blood pressure value, a pulse waveform, and a heart rate. Examples of the index for determining a degree of arteriosclerosis include a traveling time to a reflected wave (Tr) and TPP. Tr denotes a time interval between the time of appearance of an ejected wave and the time of appearance of a reflected wave which is an incident wave returning from the bifurcation of the iliac artery as a result of reflection. TPP denotes the difference between times of appearances of peaks of an ejected wave and a reflected wave.

2. Hardware Configuration

Figure 3:
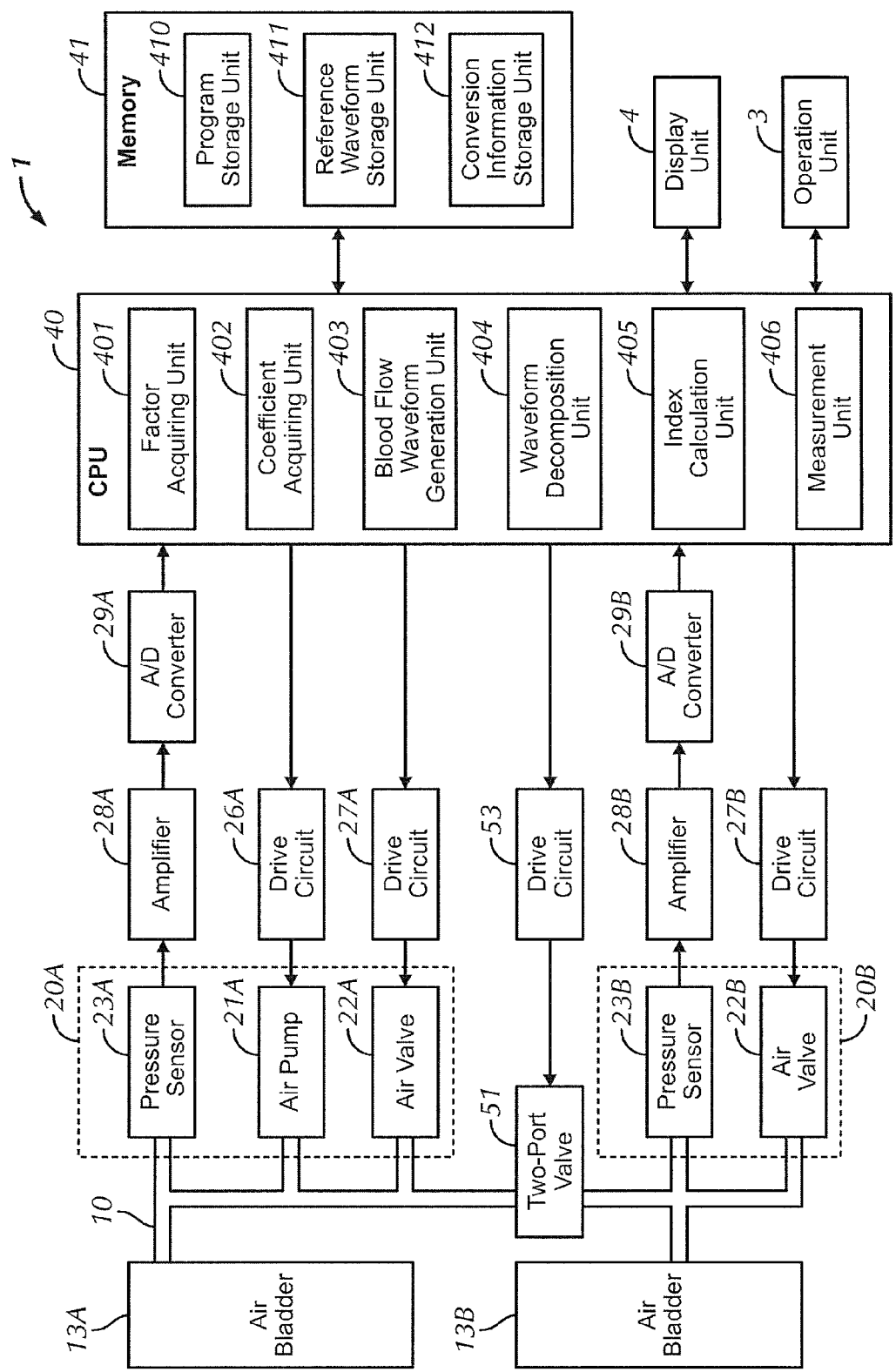
FIG. 3 is a block diagram of the blood pressure information measurement device shown in FIG. 1.

FIG. 3 illustrates functional blocks in the measurement device 1 for calculating the index of a degree of arteriosclerosis. Referring to FIG. 3, the measurement device 1 includes an air system 20A, an air system 20B and a central processing unit (CPU) 40. The air systems 20A and 20B are, respectively, connected to the air bladders 13A and 13B by air tubes 10. The air system 20A includes an air pump 21A, an air valve 22A and a pressure sensor 23A. The air system 20B includes an air valve 22B and a pressure sensor 23B.

The air pump 21A is connected to a drive circuit 26A, which is connected to the CPU 40. The air pump 21A supplies compressed gas to the air bladder 13A by being driven by the drive circuit 26A that has received an instruction from the CPU 40. As a result, the air bladder 13A is inflated.

The air valve 22A is connected to a drive circuit 27A, which is connected to the CPU 40. The air valve 22B is connected to a drive circuit 27B, which is connected to the CPU 40. The opened/closed state of the air valve 22A and the opened/closed state of the air valve 22B are, respectively, controlled by the drive circuits 27A and 27B that have received an instruction from the CPU 40. As a result of control on the opened/closed states of the air valves 22A and 22B, the air valves 22A and 22B respectively maintain the pressure in the air bladders 13A and 13B and deflate the air bladders 13A and 13B. In this way, the pressure in the air bladders 13A and 13B is controlled.

The pressure sensor 23A is connected to an amplifier 28A. The amplifier 28A is connected to an A/D converter 29A, which is connected to the CPU 40. The pressure sensor 23B is connected to an amplifier 28B. The amplifier 28B is connected to an A/D converter 29B, which is connected to the CPU 40. The pressure sensors 23A and 23B, respectively, detect the pressure in the air bladders 13A and 13B and output signals corresponding to the detected values to the amplifiers 28A and 28B. The output signals are amplified by the amplifiers 28A and 28B, digitalized by the A/D converters 29A and 29B, and then input to the CPU 40.

The air tube from the air bladder 13A and the air tube from the air bladder 13B are connected via a two-port valve 51. The two-port valve 51 is connected to a drive circuit 53, which is connected to the CPU 40. The two-port valve 51 includes a valve for the air bladder 13A and a valve for the air bladder 13B. These valves are opened and closed by the two-port valve 51 being driven by the drive circuit 53 that has received an instruction from the CPU 40.

A memory 41 includes a program storage unit 410 that stores programs executed by the CPU 40, a reference waveform storage unit 411 (described later) that stores information for identifying reference waveforms, and a conversion information storage unit 412 that stores information for converting an augmentation index (AI) value to α (described later). Note that the reference waveforms, the AI value, and α will be described later. The memory 41 also includes a storage area that serves as a work area for the CPU 40.

The CPU 40 reads programs from the memory 41 based on an instruction input to the operation unit 3 arranged on the base 2 of the measurement device, executes the read programs, and outputs control signals in accordance with the execution. The CPU 40 also outputs the results of measurement to the display unit 4 and the memory 41. The memory 41 not only stores the results of measurement, but also stores information relating to a user including at least his/her age as necessary. The CPU 40 reads this information relating to the user in accordance with execution of programs and uses the read information for processing as necessary.

The CPU 40 includes a factor acquiring unit 401, a coefficient acquiring unit 402, a blood flow waveform generation unit 403, a waveform decomposition unit 404, an index calculation unit 405, and a measurement unit 406 as functions for calculating the index of a degree of arteriosclerosis. The factor acquiring unit 401 acquires (calculates) an AI value, which is one example of factor information for a degree of arteriosclerosis. The coefficient acquiring unit 402 acquires a coefficient α, which will be described later, by converting the factor information in accordance with predetermined information. The blood flow waveform generation unit 403 generates a waveform estimated as a blood flow waveform using the coefficient α. The waveform decomposition unit 404 decomposes a pulse waveform using the blood flow waveform generated by the blood flow waveform generation unit 403. The index calculation unit 405 calculates the index of a degree of arteriosclerosis using an ejected wave and a reflected wave obtained by the waveform decomposition unit 404 decomposing the pulse waveform. The measurement unit 406 detects a pulse waveform and measures blood pressure based on control on the driving of the air pump 21A and the like and the results of detection output from the pressure sensor 23B and the like. These are functions that are configured mainly by the CPU 40 reading and executing programs stored in the memory 41 in accordance with operation signals from the operation unit 3. At least a part of these functions may be configured in the form of a hardware configuration.

3. Stored Information (3-1. Reference Waveforms)

Figure 4:
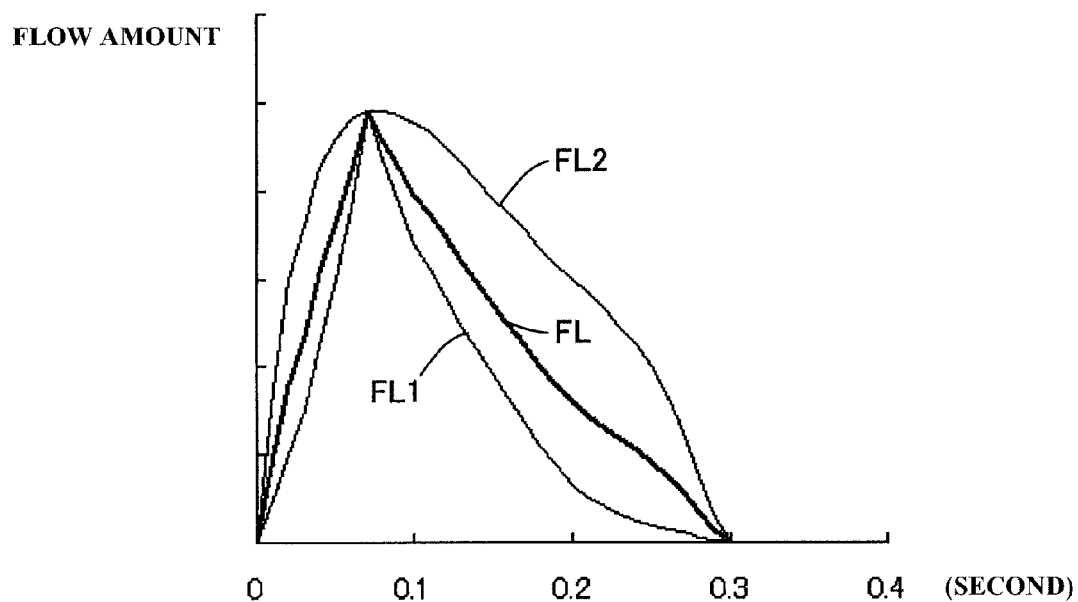
FIG. 4 illustrates information stored in a reference waveform storage unit shown in FIG. 3.

FIG. 4 shows reference waveforms identified by information stored in the reference waveform storage unit 411.

A graph shown in FIG. 4 includes a first reference waveform FL1 and a second reference waveform FL2.

Information for identifying the first reference waveform FL1 and the second reference waveform FL2 is predetermined information that is stored in the reference waveform storage unit 411 at the time of, for example, factory shipment of the measurement device 1.

Note that the first reference waveform FL1 corresponds to the case of elderly people and the like who are considered to have a relatively high degree of arteriosclerosis. The second reference waveform FL2 corresponds to the case of young people and the like who are considered to have a relatively low degree of arteriosclerosis.

It is considered that the aforementioned error in the calculation of Tr according to the method disclosed in Patent Literature 2 is attributed to the difference between a triangle waveform and an actual blood flow waveform. Furthermore, as described in Non-Patent Literature 1, while a blood flow waveform of measurement subjects with a high degree of arteriosclerosis, such as elderly people, has a sharp vertex, a blood flow waveform of young measurement subjects with a low degree of arteriosclerosis has a round vertex. The inventors of embodiments of the present invention consider that one of the reasons why there is error in the calculation of Tr is because every blood flow waveform is uniformly approximated using a triangle waveform even though different measurement subjects exhibit different blood flow waveforms.

In the present embodiment, a pulse waveform is detected, an AI value is calculated from the pulse waveform, and the AI value is converted to a coefficient $\alpha$. A blood flow waveform FL of a measurement subject is estimated by compositing the first reference waveform FL1 and the second reference waveform FL2 in accordance with the following expression A using the coefficient $\alpha$.

$$FL=FL1+(FL2-FL1)\times\alpha \qquad \text{Expression A}$$

FIG. 4 shows the first reference waveform FL1, the second reference waveform FL2, and an example of the blood flow waveform FL generated by compositing the first reference waveform FL1 and the second reference waveform FL2 in accordance with the expression A.
(3-2. Information for Conversion)

Figure 5:
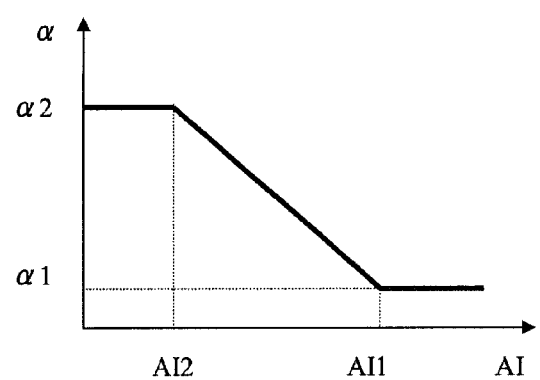
FIG. 5 illustrates information stored in a conversion information storage unit shown in FIG. 3.

FIG. 5 shows a relationship between AI and the coefficient $\alpha$ identified by information stored in the conversion information storage unit 412. As can be understood from FIG. 5, the coefficient $\alpha$ takes any value from $\alpha1$ to $\alpha2$ ($0\leq\alpha1<\alpha2\leq1$) and is a function of AI that can be expressed by the following expressions B1 to B3. Note that a and b in the following expression B2 are predetermined coefficients. Also, AI1 and AI2 are predetermined AI values.

$$\text{When } AI<AI2: \alpha=\alpha2 \qquad \text{Expression B1}$$

$$\text{When } AI2\leq AI<AI1: \alpha=AI\times a+b \qquad \text{Expression B2}$$

$$\text{When } AI1<AI: \alpha=\alpha1 \qquad \text{Expression 3}$$

When the coefficient $\alpha$ is determined in the above manner, the larger the value of AI, the smaller the value of $\alpha$. Therefore, according to the blood flow waveform FL generated in accordance with the expression A, the larger the value of AI, the larger the contribution of the waveform corresponding to the case where a degree of arteriosclerosis is considered to be relatively high (the first reference waveform FL1), and the smaller the contribution of the waveform corresponding to the case where a degree of arteriosclerosis is considered to be relatively low (the second reference waveform FL2).

4. Arteriosclerosis Index Calculation Processing

Figure 6:
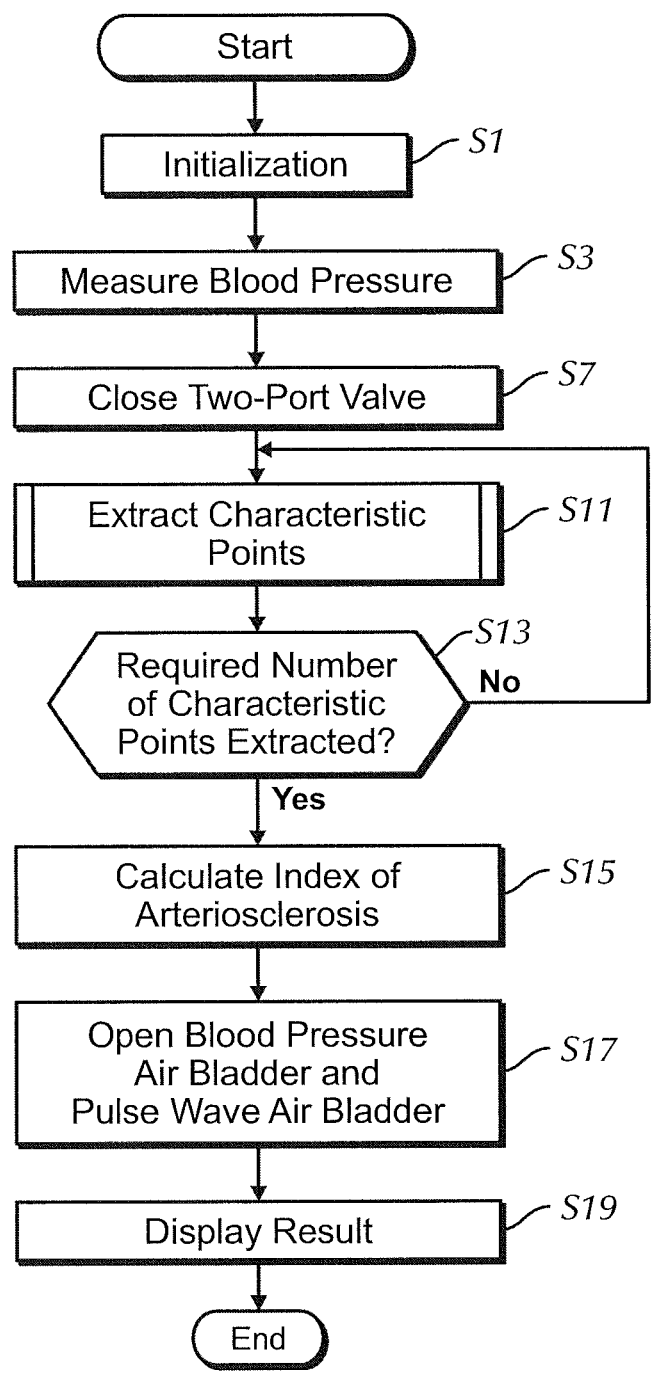
FIG. 6 is a flowchart of arteriosclerosis index calculation processing executed by the blood pressure information measurement device shown in FIG. 1.

The following describes processing executed by the measurement device 1 to calculate the index relating to a degree of arteriosclerosis (arteriosclerosis index calculation processing) with reference to FIG. 6, which shows a flowchart of this processing.
(4-1. Adjustment of Cuff Pressure)

Figure 8A:
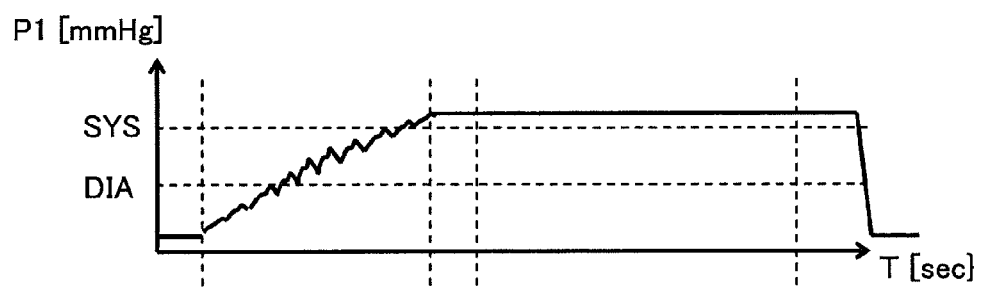
FIGS. 8A and 8B show changes in the pressure in operating air bladders of the blood pressure information measurement device shown in FIG. 1.
Figure 8B:
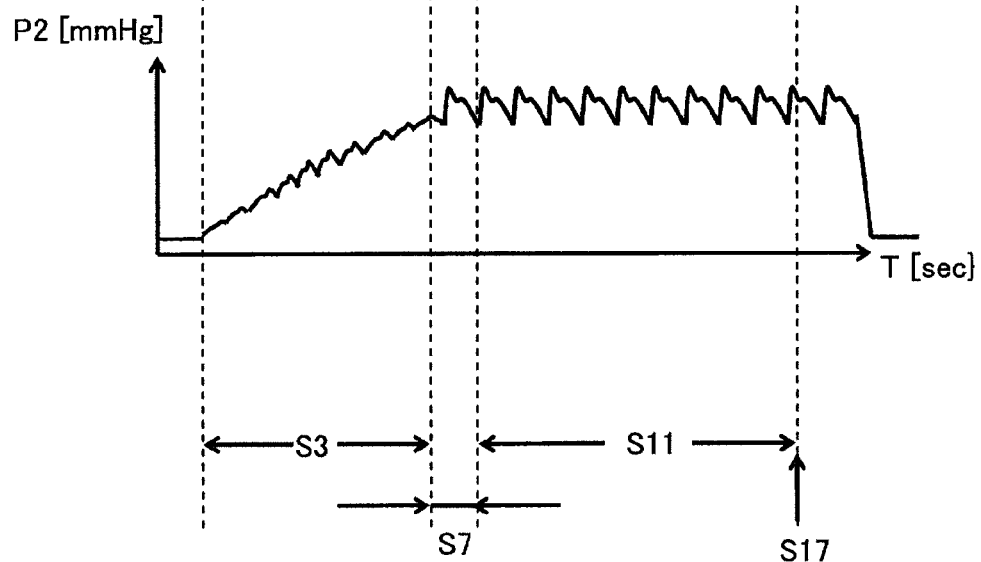

The operation shown in FIG. 6 is started when a user presses the switch 32. This operation is realized by the CPU 40 reading a program stored in the memory 41 and controlling the components shown in FIG. 3. FIGS. 8A and 8B show changes in the internal pressure P1 of the air bladder 13A and the internal pressure P2 of the air bladder 13B caused by the measurement operation.

Referring to FIG. 6, once the operation has been started, the CPU 40 initializes each component in step S1. In step S3, the measurement unit 406 starts to inflate the air bladder 13A by outputting a control signal to the air system 20A, and measures blood pressure during the process of inflation. Note that in step S3, blood pressure is measured using an oscillometric method that is used in general blood pressure monitors.

After both valves of the two-port valve 51 are opened in the initialization process of step S1, the compressed air is supplied by the pump 21 in step S3, thereby increasing the internal pressure P1 of the air bladder 13A and the internal pressure P2 of the air bladder 13B as illustrated as a time period S3 in FIGS. 8A and 8B.

Upon completion of the measurement of blood pressure in step S3, the CPU 40 outputs a control signal to the drive circuit 53 so as to close both valves of the two-port valve 51 in S7. As a result, the space in the air bladder 13A and the space in the air bladder 13B are separated from each other. Note that in step S3, the internal pressure P1 of the air bladder 13A is increased to a pressure higher than a systolic blood pressure value. Therefore, at this point, the air bladder 13A is restricting blood flow in a site on the distal side of the site around which the air bladder 13B used for measuring a pulse wave is wrapped. That is to say, the air bladder 13A is functioning as a compression air bladder.
(4-2. Extraction of Characteristic Points)

While blood flow is restricted in the site on the distal side, each time a pulse waveform corresponding to one heartbeat based on a pressure signal from the pressure sensor 23B is input, the measurement unit 406 performs an operation for extracting a characteristic point from the pulse waveform in step S11. A process for this operation is described below with reference to FIG. 7, which shows a subroutine of step S11.
(4-3. Estimation of Blood Flow Waveform)

Figure 7:
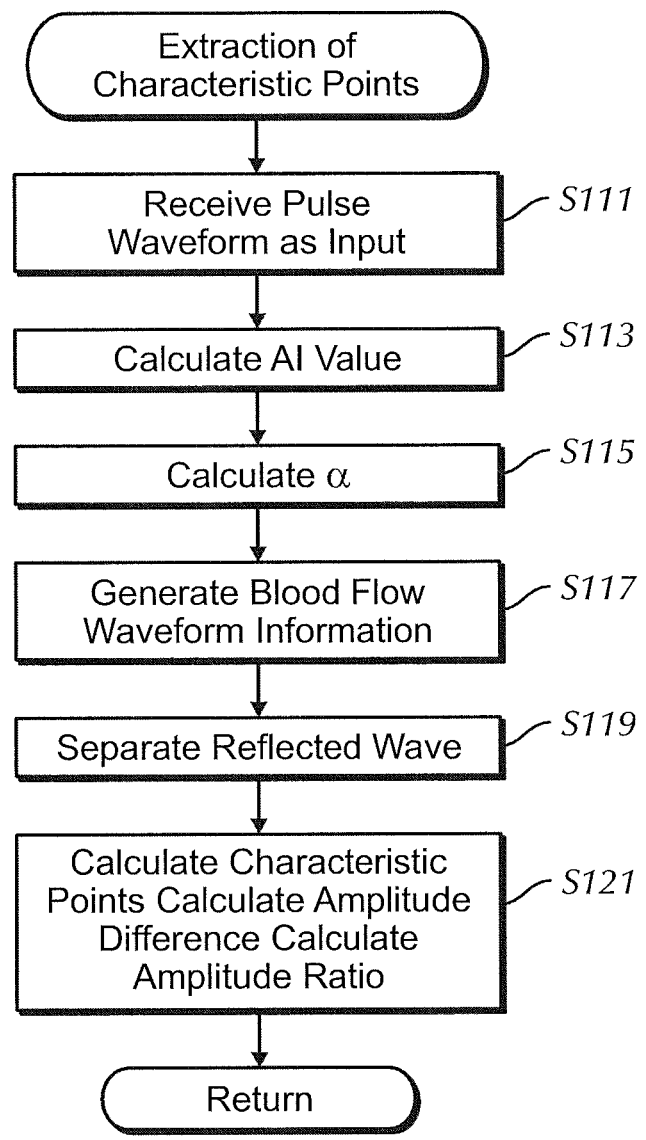
FIG. 7 is a flowchart of a subroutine of a characteristic point extraction process shown in FIG. 6.

Referring to FIG. 7, while blood flow is restricted in the portion on the distal side, the factor acquiring unit 401 receives, as input, a pulse waveform corresponding to one heartbeat based on a pressure signal from the pressure sensor 23B in step S111. The factor acquiring unit 401 then proceeds to the process of step S113.

Figure 9A:
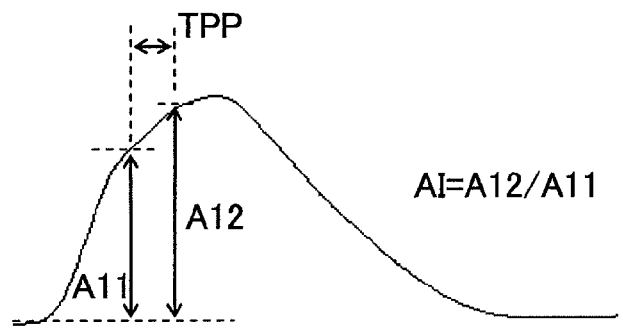
FIG. 9A illustrates calculation of an augmentation index (AI) from a pulse waveform detected by the blood pressure information measurement device shown in FIG. 1.
Figure 9B:
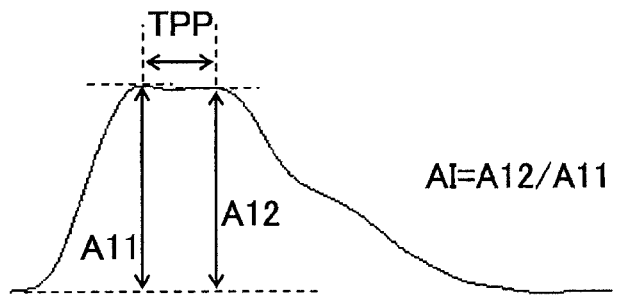
FIG. 9B illustrates calculation of AI from a pulse waveform detected by the blood pressure information measurement device shown in FIG. 1.
Figure 9C:
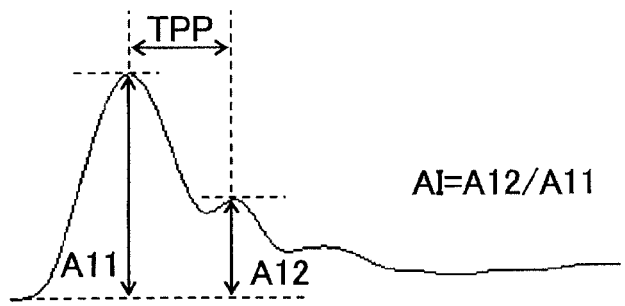
FIG. 9C illustrates calculation of AI from a pulse waveform detected by the blood pressure information measurement device shown in FIG. 1.

In step S113, the factor acquiring unit 401 calculates an AI value using the pulse waveform corresponding to one heartbeat acquired in step S111. The AI value can be calculated by, for example, calculating the amplitude ratio between an ejected wave and a reflected wave in the pulse waveform corresponding to one heartbeat. FIGS. 9A to 9C show examples of AI calculated in step S113. As can be understood from FIGS. 9A to 9C, AI is calculated as, for example, a ratio of an amplitude value (A12) of a reflected wave to an amplitude value (A11) of an ejected wave.

Next, in step S115, the coefficient acquiring unit 402 calculates a coefficient $\alpha$ using the AI value calculated in step S113 and information stored in the conversion information storage unit 412 in the manner described earlier.

Subsequently, in step S117, the blood flow waveform generation unit 403 generates an estimated blood flow waveform FL using the coefficient $\alpha$, the first reference waveform FL1 and the second reference waveform FL2 in accordance with the aforementioned expression A.
(4-4. Decomposition of Pulse Waveform into Ejected Wave and Reflected Wave)

Next, in step S119, the waveform decomposition unit 404 decomposes the pulse waveform input in step S111 into an ejected wave and a reflected wave using the blood flow waveform FL generated in step S117. This decomposition may be performed using any known method, e.g. a method disclosed in Patent Literature 2.

Regarding the decomposition of the pulse waveform, a description is now given of the premise thereof.

A blood pressure waveform (Pm) is expressed as a sum of an ejected wave (Pf) and a reflected wave (Pb) (expression 1). A blood flow waveform (Fm) is expressed as a sum of an ejected wave (Ff) and a reflected wave (Fb) (expression 2). A relationship between blood pressure and blood flow defines the characteristic impedance (Zc) equivalent to vascular resistance. The relationships of the following expressions 3 and 4 hold with the characteristic impedance (Zc).

$Pm=Pf+Pb$      Expression 1

$Fm=Ff+Fb$      Expression 2

$Pf=Zc \times Ff$      Expression 3

$Pb=Zc \times Fb$      Expression 4

Regarding the ejected wave (Pf) and the reflected wave (Pb), the following expressions 5 and 6 can be derived based on the relationships of the expressions 1 to 4.

$Pf=Zc \times Ff=(Pm+Zc \times Fm)/2$      Expression 5

$Pb=-Zc \times Fb=(Pm-Zc \times Fm)/2$      Expression 6

Note that Zc is calculated using the fast Fourier transforms for the blood pressure waveform (Pm) and the blood flow waveform (Fm) in accordance with the following expression 7.

$Zc=|Z|=|FFT(Pm)|/|FFT(Fm)|$      Expression 7

Waveforms of the ejected wave (Pf) and the reflected wave (Pb) in the blood pressure waveform (Pm) are generated by using the blood flow waveform generated in step S117 as Fm in the above expressions 5 to 7. As a result, the pulse waveform is decomposed into the ejected wave and the reflected wave.

(4-5. Calculation of Index of Arteriosclerosis)

In step S121, the index calculation unit 405 calculates the start point (characteristic point) of the reflected wave in the pulse waveform based on the decomposition of the pulse waveform in step S119, calculates the amplitude difference between the ejected wave and the reflected wave, and calculates the amplitude ratio between the ejected wave and the reflected wave. Thereafter, the index calculation unit 405 returns to the processing of FIG. 6.

When the number of sets of the characteristic point, amplitude difference and amplitude ratio calculated in step S121 has reached a predetermined number (corresponding to, for example, ten heartbeats) (the YES branch of step S13), the CPU 40 proceeds to the process of step S15.

In step S15, the index calculation unit 405 calculates Tr, TPP, or the like as the index of a degree of arteriosclerosis using the average values of the aforementioned characteristic points, amplitude differences and amplitude ratios.

(4-6. Display of Information)

In step S17, the CPU 40 outputs control signals to the drive circuits 27A and 27B so as to open the air valves 22A and 22B, thereby releasing the pressure in the air bladders 13A and 13B to the atmosphere. In the examples of FIGS. 8A and 8B, after step S17, the pressure P1 and the pressure P2 are rapidly decreased to the atmospheric pressure.

The calculated systolic blood pressure value (SYS), diastolic blood pressure value (DIA) and index of a degree of arteriosclerosis, as well as the result of measurement such as the measured pulse wave, are displayed on the display unit 4 arranged on the base 2 after being subjected to processing for such display.

According to one or more embodiments of the present invention, an estimated blood flow waveform is generated using predetermined waveforms instead of approximating a blood flow waveform using a triangle waveform as disclosed in Patent Literature 2. According to one or more embodiments of the present invention, a blood flow waveform is generated by compositing a plurality of waveforms using a coefficient related to a factor that is considered to affect a degree of arteriosclerosis. As a result, the shape of the generated blood flow waveform can be changed in a stepwise fashion from the shape having a sharp vertex to the shape having a round vertex. This allows for approximation to the shape that is similar to an actual blood flow waveform of the measurement subject. Accordingly, approximation of a blood flow waveform can be performed correctly compared to when a triangle waveform is used, with the result that a pulse waveform can be decomposed in a more correct manner.

5. Tr in Present Embodiment

Figure 10:
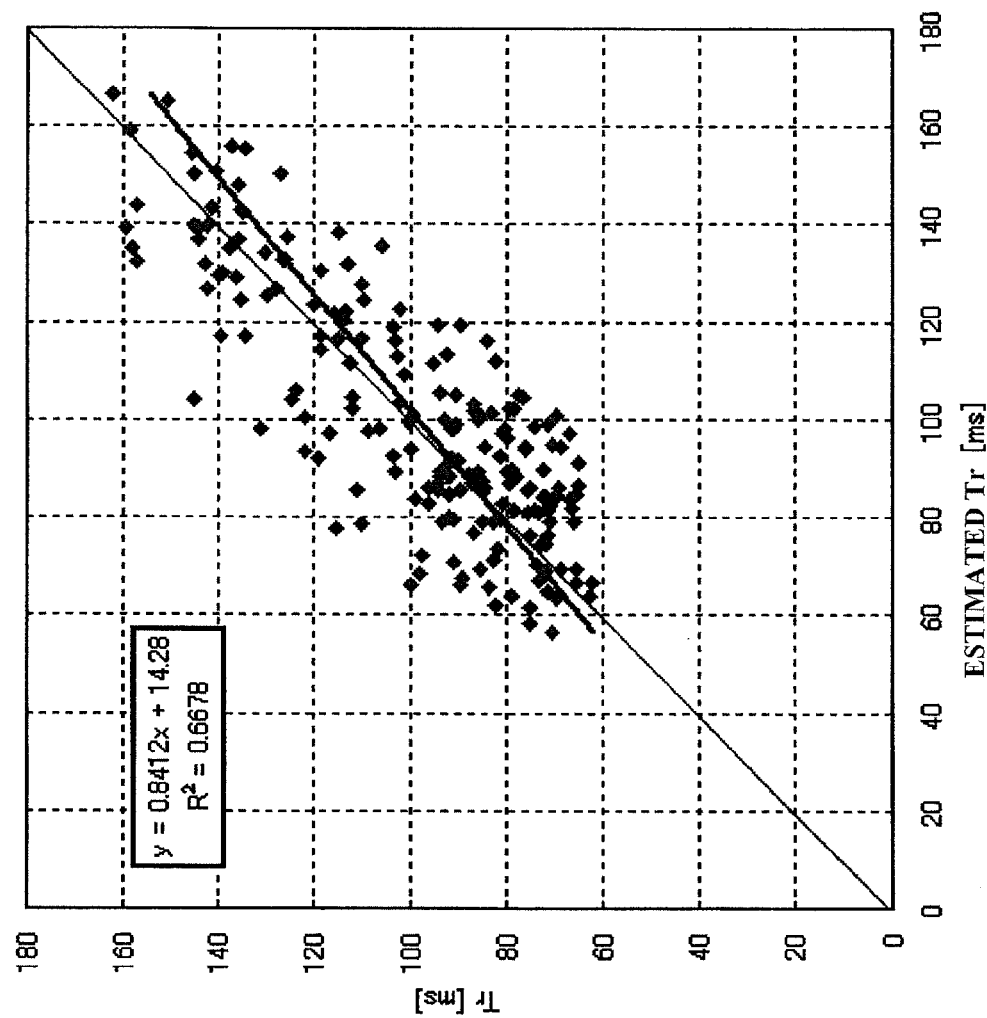
FIG. 10 shows Tr calculated by the blood pressure information measurement device shown in FIG. 1.

FIG. 10 shows Tr calculated in the present embodiment. In FIG. 10, a vertical axis represents Tr calculated in accordance with the present embodiment, and a horizontal axis represents estimated Tr values based on PWV between the heart and the femoral artery.

As can be understood from FIG. 10, the square of the correlation function between Tr calculated in accordance with the present embodiment and the estimated values based on PWV ($R^2$) is 0.6678. Therefore, it can be said that the present embodiment allows calculating Tr with high accuracy compared to conventional technology.

6. Modification Example 1

In the present embodiment described above, an AI value calculated from a pulse waveform is used as information on factors that affect arteriosclerosis. However, the factor information according to one or more embodiments of the present invention is not limited to the AI value.

For example, a TPP value calculated from a pulse waveform may be used as the factor information.

Figure 11:
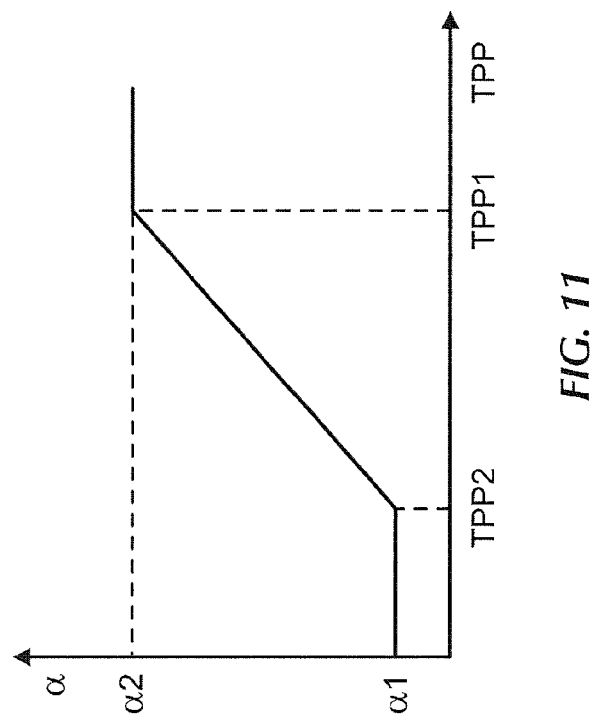
FIG. 11 illustrates information stored in a conversion information storage unit according to Modification Example (1) of the blood pressure information measurement device shown in FIG. 1.

FIG. 11 shows a relationship between TPP and a coefficient α identified by information stored in the conversion information storage unit 412 in the present modification example. As can be understood from FIG. 11, the coefficient α takes any value from α1 to α2 ($0 \leq \alpha 1 < \alpha 2 \leq 1$) and is a function of TPP that can be expressed by the following expressions C1 to C3. Note that a1 and b1 in the following expression C2 are predetermined coefficients. Also, TPP1 and TPP2 are predetermined TPP values.

When $TPP < TPP2$: $\alpha = \alpha 1$      Expression C1

When $TPP2 \leq TPP < TPP1$: $\alpha = Tr \times a1 + b1$      Expression C2

When $TPP1 < TPP$: $\alpha = \alpha 2$      Expression C3

Figure 12:
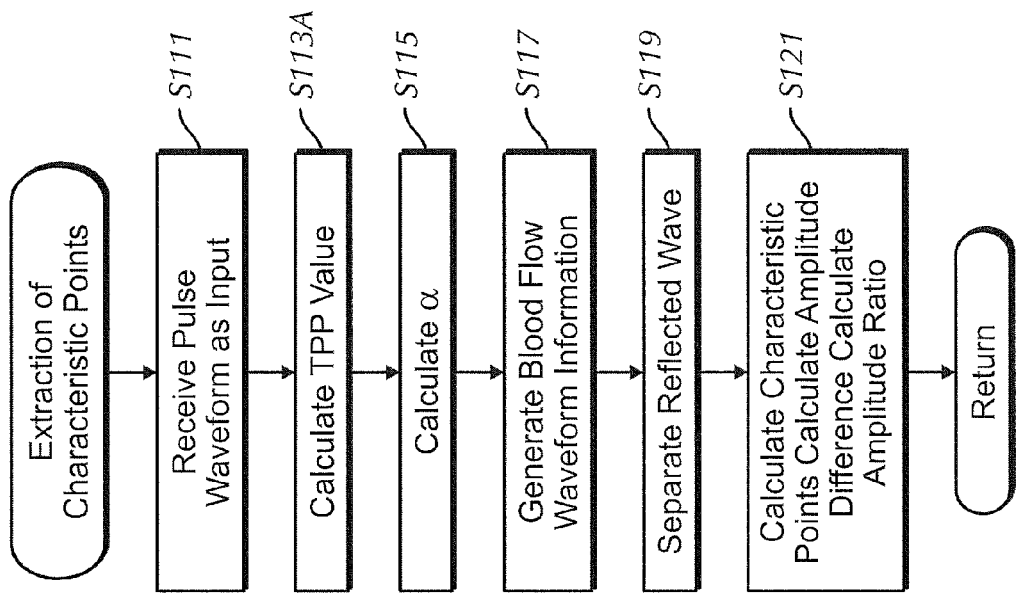
FIG. 12 is a flowchart of a subroutine of a characteristic point extraction process according to Modification Example (1) of the blood pressure information measurement device shown in FIG. 1.

In the present modification example, step S113A shown in FIG. 12 is executed in place of step S113 shown in FIG. 7. In step S113A shown in FIG. 12, the factor acquiring unit 401 calculates TPP from the pulse waveform input in step S111. The factor acquiring unit 401 calculates TPP by, for example, calculating the difference between times of peaks of the ejected wave and the reflected wave that have been described with reference to FIG. 9A and the like.

In step S115, the coefficient acquiring unit 402 converts TPP to a using the information that has been described with reference to FIG. 11.

When the coefficient α is determined in the above manner, the larger the value of TPP, the larger the value of α. Therefore, according to the blood flow waveform FL generated in accordance with the expression A, the larger the value of TPP, the smaller the contribution of the waveform corresponding to the case where a degree of arteriosclerosis is considered to be relatively high (the first reference waveform FL1), and the larger the contribution of the waveform corresponding to the case where a degree of arteriosclerosis is considered to be relatively low (the second reference waveform FL2).

7. Modification Example 2

A Tr value calculated from a pulse waveform may be used as the factor information.

Figure 13:
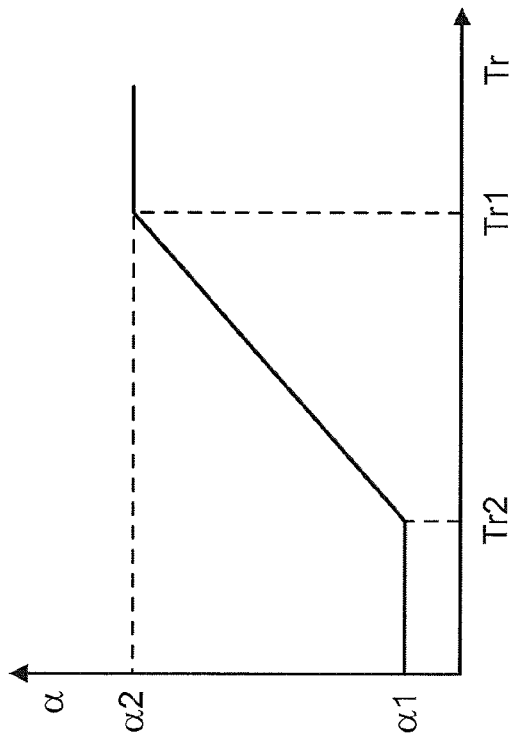
FIG. 13 illustrates information stored in a conversion information storage unit according to Modification Example (2) of the blood pressure information measurement device shown in FIG. 1.

FIG. 13 shows a relationship between Tr and a coefficient α identified by information stored in the conversion information storage unit 412 in the present modification example. As can be understood from FIG. 13, the coefficient α takes any value from α1 to α2 ($0 \leq \alpha1 < \alpha2 < 1$) and is a function of Tr that can be expressed by the following expressions D1 to D3. Note that a2 and b2 in the following expression D2 are predetermined coefficients. Also, Tr1 and Tr2 are predetermined Tr values.

When $Tr < Tr2$: $\alpha = \alpha1$ \hfill Expression D1

When $Tr2 \leq Tr < Tr1$: $\alpha = Tr \times a2 + b2$ \hfill Expression D2

When $Tr1 < Tr$: $\alpha = \alpha2$ \hfill Expression D3

Figure 14:
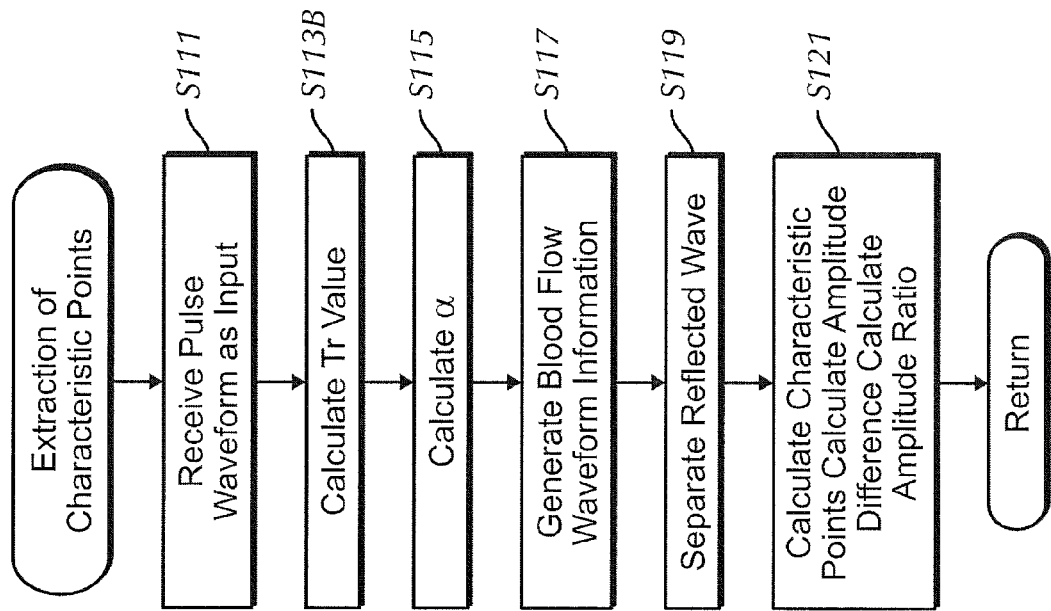
FIG. 14 is a flowchart of a subroutine of a characteristic point extraction process according to Modification Example (2) of the blood pressure information measurement device shown in FIG. 1.

In the present modification example, step S113B shown in FIG. 14 is executed in place of step S113 shown in FIG. 7. In step S113B shown in FIG. 14, the factor acquiring unit 401 calculates Tr from the pulse waveform input in step S111. The factor acquiring unit 401 calculates Tr in accordance with, for example, known technology such as technology using the fourth derivative of the pulse waveform.

In step S115, the coefficient acquiring unit 402 converts Tr to α using the information that has been described with reference to FIG. 13.

When the coefficient α is determined in the above manner, the larger the value of Tr, the larger the value of α. Therefore, according to the blood flow waveform FL generated in accordance with the expression A, the larger the value of Tr, the smaller the contribution of the waveform corresponding to the case where a degree of arteriosclerosis is considered to be relatively high (the first reference waveform FL1), and the larger the contribution of the waveform corresponding to the case where a degree of arteriosclerosis is considered to be relatively low (the second reference waveform FL2).

8. Modification Example 3

The age of the measurement subject may be used as the factor information.

Figure 15:
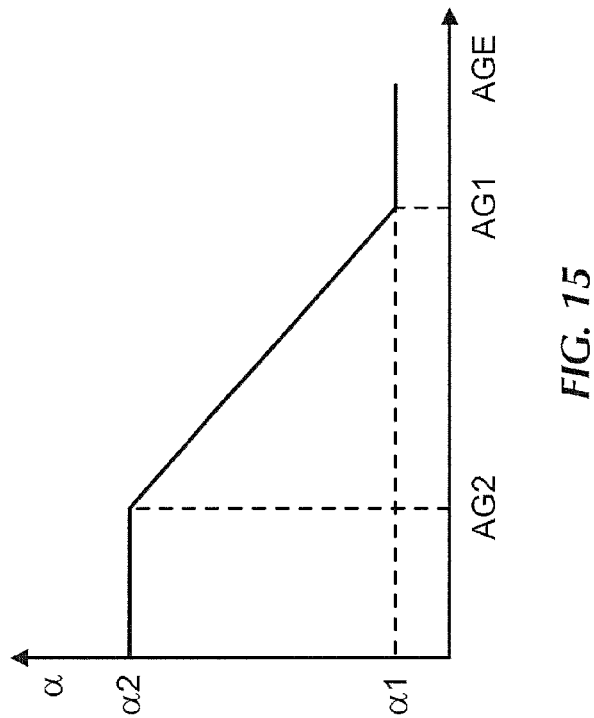
FIG. 15 illustrates information stored in a conversion information storage unit according to Modification Example (3) of the blood pressure information measurement device shown in FIG. 1.
Figure 17B:
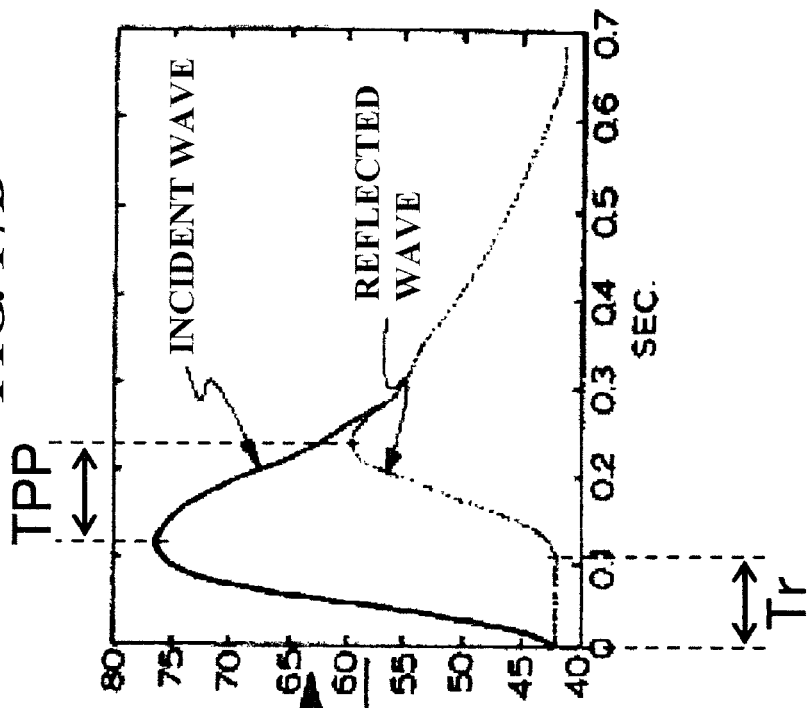
FIGS. 17A and 17B illustrate conventional technology.
Figure 17A:
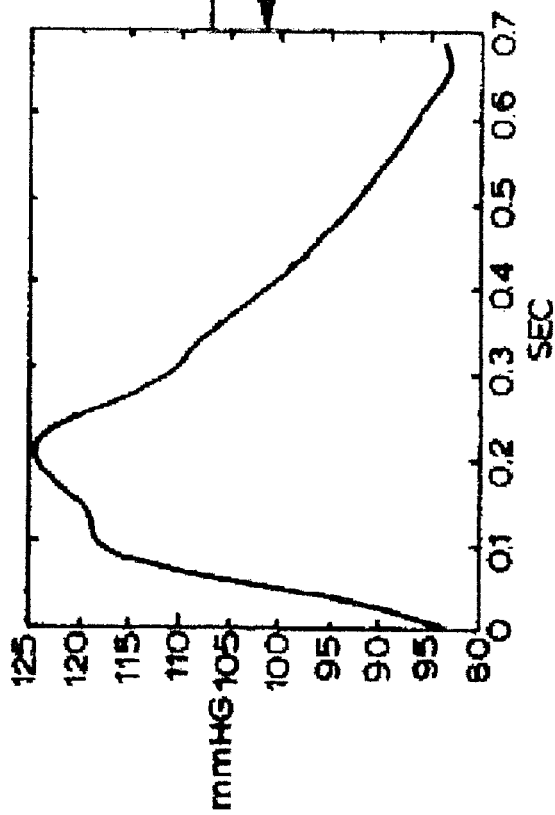
Figure 18:
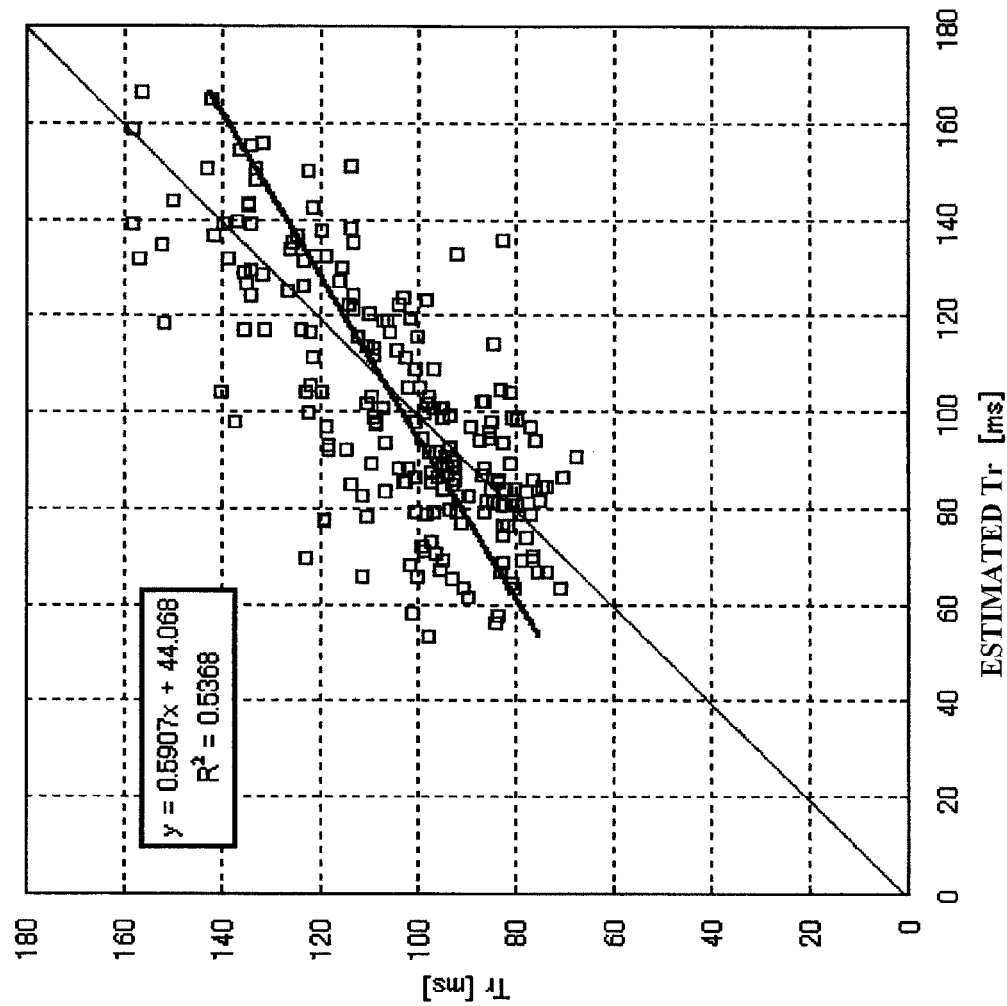
FIG. 18 shows Tr calculated in accordance with conventional technology.

FIG. 15 shows a relationship between the age AG of the measurement subject and a coefficient α identified by information stored in the conversion information storage unit 412 in the present modification example. As can be understood from FIG. 15, the coefficient α takes any value from α1 to α2 ($0 \leq \alpha1 < \alpha2 \leq 1$) and is a function of Tr that can be expressed by the following expressions E1 to E3. Note that a3 and b3 in the following expression E2 are predetermined coefficients. Also, AG1 and AG2 are predetermined values related to the age.

When $AG < AG2$: $\alpha = \alpha2$ \hfill Expression E1

When $AG2 \leq AG < AG1$: $\alpha = AG \times a3 + b3$ \hfill Expression E2

When $AG1 < Tr$: $\alpha = \alpha1$ \hfill Expression E3

Figure 16:
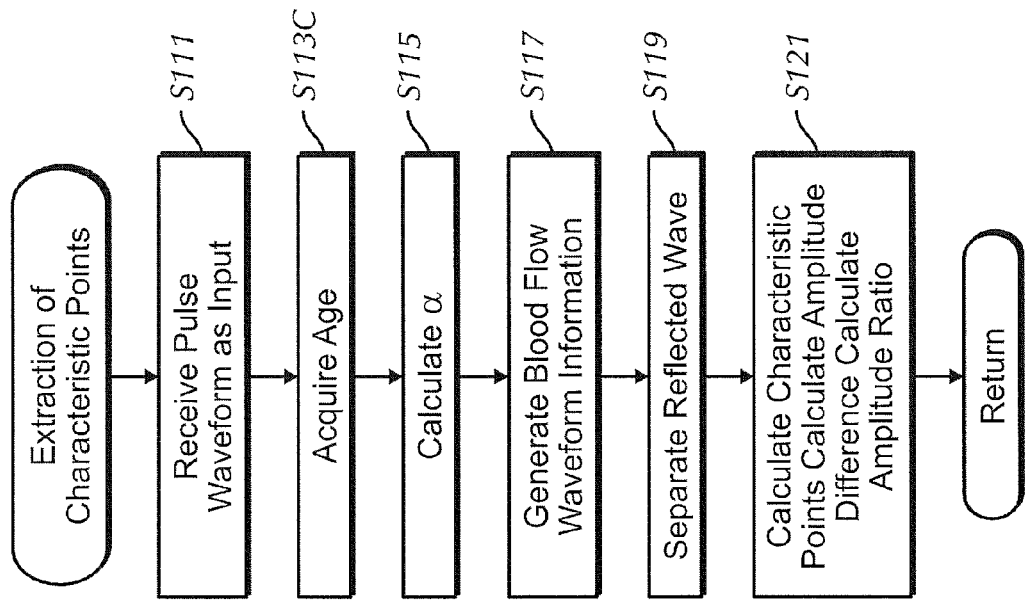
FIG. 16 is a flowchart of a subroutine of a characteristic point extraction process according to Modification Example (3) of the blood pressure information measurement device shown in FIG. 1.

In the present modification example, step S113C shown in FIG. 16 is executed in place of step S113 shown in FIG. 7. In step S113C shown in FIG. 16, the factor acquiring unit 401 acquires the age of the measurement subject. The age of the measurement subject is input via, for example, the operation unit 3.

In step S115, the coefficient acquiring unit 402 converts AG to α using the information that has been described with reference to FIG. 15.

When the coefficient α is determined in the above manner, the larger the value of AG, the smaller the value of α. Therefore, according to the blood flow waveform FL generated in accordance with the expression A, the older the measurement subject, the larger the contribution of the waveform corresponding to the case where a degree of arteriosclerosis is considered to be relatively high (the first reference waveform FL1), and the smaller the contribution of the waveform corresponding to the case where a degree of arteriosclerosis is considered to be relatively low (the second reference waveform FL2).

9. Modification Example 4

With the measurement device 1, the measurement site of the measurement subject on which the arm band 9 that includes the pressure sensor 23B is worn is the arm. However, the measurement site by the blood pressure information measurement device according to one or more embodiments of the present invention is not limited to the arm, but may be the neck. Such a blood pressure information measurement device may use, for example, a carotid pulse wave detection device disclosed in JP 10-309266A as a detection member and detection means. This device includes: a carotid pulse wave sensor that detects a pulse wave from the carotid artery of a live body by being pressed against the carotid artery; a support member that supports the carotid pulse wave sensor; a contact member that is joined to the support member and comes in contact with an area opposite to the area being pressed by the carotid pulse wave sensor out of the outer circumferential surface of the neck of the live body; and a holding device which is curved as a whole in a plane so as to hold the neck of the live body and in which the support member and the contact member are biased by a resilient restoring force in a direction in which they approach each other while the live body is wearing the holding device.

10. Other Modification Examples, Etc.

In the above-described embodiment, α is determined based on the AI value, Tr value, TPP value, or age of the measurement subject. Alternatively, α may be calculated by weighting and combining sets of α that are calculated based on the AI value, Tr value, TPP value and age in accordance with the aforementioned methods. That is to say, provided that α calculated based on the AI value is α1, α calculated based on the Tr value is α2, α calculated based on the TPP value is α3, and α calculated based on the age is α4, α may be calculated using the following expression 8.

$$\alpha = p\alpha 1 + q\alpha 2 + r\alpha 3 + k\alpha 4 \qquad \text{Expression 8}$$

Note that coefficients p, q, r and k in the expression 8 are values used for weighting the AI value, Tr value, TPP value and age, respectively, and may be set as appropriate.

Alternatively, α may be calculated by combining two or three selected from the group of α1, α2, α3 and α4 in accordance with weights, instead of combining all of α1, α2, α3 and α4.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

According to one or more embodiments of the present invention, a blood flow waveform for decomposing a pulse waveform into an ejected wave and a reflected wave is estimated by compositing a plurality of pseudo blood flow waveforms using a coefficient obtained from factor information for a degree of arteriosclerosis. As a result, the blood pressure waveform can be decomposed into the ejected wave and the reflected wave in a more correct manner.

REFERENCE NUMERALS LIST 1 measurement device
2 base
3 operation uni
9 cuff
10 air tube
13A,13B air bladder
20A,20B air system
21A,21B air pump
22A,22B air valve
23A,23B pressure sensor
27A,27B drive circuit
28A,28B amplifier
29A,29B A/D converter
31,32 switch
40 central processing unit (CPU)
41 memory
51 two-port valve
53 drive circuit

The invention claimed is:

1. A blood pressure information measurement device for calculating an index of a degree of arteriosclerosis of a measurement subject as blood pressure information, comprising:
  a detection member comprising a plurality of pressure sensors;
  a central processing unit that detects a pulse waveform by bringing the detection member into contact with an exterior of a measurement site of the measurement subject, wherein the central processing unit:
    acquires factor information for the degree of arteriosclerosis;
    converts the factor information to a coefficient α, the coefficient α being a function of the factor information;
    stores a first reference waveform and a second reference waveform;
    generates a waveform estimated as a blood flow waveform by compositing the first reference waveform and the second reference waveform using the coefficient α;
    decomposes the pulse waveform into waveforms of an ejected wave and a reflected wave using the pulse waveform and the waveform estimated as the blood flow waveform; and
    calculates the index of the degree of arteriosclerosis from a relationship between the ejected wave and the reflected wave obtained by decomposing the pulse waveform; and
  a display that displays the index of the degree of arteriosclerosis.

2. The blood pressure information measurement device according to claim 1, wherein the factor information is at least one from the group consisting of: an augmentation index (AI) value, a difference between times of appearances of the ejected wave and the reflected wave, and a difference between times of peaks of the ejected wave and the reflected wave calculated from the pulse waveform.

3. The blood pressure information measurement device according to claim 1,
  wherein the detection member comprises a first air bladder for compressing a measurement site and a second air bladder for compressing a measurement site located on the distal side of the first air bladder, and
  wherein the central processing unit detects the pulse waveform based on changes in an internal pressure of the first air bladder while blood flow is restricted using the second air bladder.

4. The blood pressure information measurement device according to claim 1, wherein the factor information comprises an age of the measurement subject.

5. The blood pressure information measurement device according to claim 1, wherein the central processing unit detects the pulse waveform by detecting a pressure waveform measured in a brachial artery.

6. The blood pressure information measurement device according to claim 1, wherein the central processing unit detects the pulse waveform by detecting a pressure waveform measured in a radial artery.

7. The blood pressure information measurement device according to claim 1, wherein the central processing unit detects the pulse waveform by detecting a pressure waveform measured in a carotid artery.

8. A method for calculating an index of a degree of arteriosclerosis of a measurement subject as blood pressure information in a blood pressure information measurement device, comprising:
  detecting a pulse waveform by bringing a detection member comprising a plurality of pressure sensors into contact with an exterior of a measurement site of the measurement subject;
  acquiring factor information for the degree of arteriosclerosis;
  converting the factor information to a coefficient α, the coefficient α being a function of the factor information;
  storing a first reference waveform and a second reference waveform;
  generating a waveform estimated as a blood flow waveform by compositing the first reference waveform and the second reference waveform using the coefficient α;
  decomposing the pulse waveform into waveforms of an ejected wave and a reflected wave using the pulse waveform and the waveform estimated as the blood flow waveform;

calculating the index of the degree of arteriosclerosis from a relationship between the ejected wave and the reflected wave obtained by decomposing the pulse waveform; and displaying the index of the degree of arteriosclerosis.

9. The blood pressure information measurement device according to claim 2, wherein the detection member comprises a first air bladder for compressing a measurement site and a second air bladder for compressing a measurement site located on the distal side of the first air bladder, and wherein the central processing unit detects the pulse waveform based on changes in an internal pressure of the first air bladder while blood flow is restricted using the second air bladder.

10. The blood pressure information measurement device according to claim 2, wherein the factor information comprises an age of the measurement subject.

11. The blood pressure information measurement device according to claim 2, wherein the central processing unit detects the pulse waveform by detecting a pressure waveform measured in a brachial artery.

12. The blood pressure information measurement device according to claim 2, wherein the central processing unit detects the pulse waveform by detecting a pressure waveform measured in a radial artery.

13. The blood pressure information measurement device according to claim 2, wherein the central processing unit detects the pulse waveform by detecting a pressure waveform measured in a carotid artery.

* * * * *